(12) United States Patent
Usher et al.

(10) Patent No.: US 11,339,627 B2
(45) Date of Patent: May 24, 2022

(54) METHOD OF ESTABLISHING A CEMENT PLUG IN AN ANNULAR REGION BETWEEN A FIRST AND A SECOND CASING

(71) Applicant: Well-Set P&A AS, Stavanger (NO)

(72) Inventors: Craig Usher, Inverclyde (GB); Nader Behjat, Stavanger (NO); Grant Knight, Stavanger (NO)

(73) Assignee: Well-Set P&A AS, Stavanger (NO)

( * ) Notice: Subject to any disclaimer, the term of this patent is extended or adjusted under 35 U.S.C. 154(b) by 113 days.

(21) Appl. No.: 16/484,544

(22) PCT Filed: Feb. 8, 2018

(86) PCT No.: PCT/NO2018/050035
§ 371 (c)(1),
(2) Date: Aug. 8, 2019

(87) PCT Pub. No.: WO2018/147745
PCT Pub. Date: Aug. 16, 2018

(65) Prior Publication Data
US 2020/0032614 A1    Jan. 30, 2020

(30) Foreign Application Priority Data

Feb. 8, 2017   (NO) .................................. 20170196
Jun. 9, 2017   (NO) .................................. 20170944

(51) Int. Cl.
*E21B 33/134*   (2006.01)
*E21B 33/12*    (2006.01)
(Continued)

(52) U.S. Cl.
CPC ........ *E21B 33/134* (2013.01); *E21B 33/1204* (2013.01); *C09K 8/426* (2013.01); *G01N 33/383* (2013.01)

(58) Field of Classification Search
CPC .... E21B 33/13; E21B 33/134; E21B 33/1204; C09K 8/42; C09K 8/426; G01N 33/383
See application file for complete search history.

(56) References Cited

U.S. PATENT DOCUMENTS

| 4,802,534 A | 2/1989 | Larson et al. |
| 2014/0224480 A1 | 8/2014 | Nguyen et al. |

(Continued)

FOREIGN PATENT DOCUMENTS

| EP | 2192263 | 6/2010 |
| SU | 641074 | 1/1979 |

(Continued)

OTHER PUBLICATIONS

International Search Report for PCT/NO2018/050035, dated May 4, 2018.

(Continued)

*Primary Examiner* — Crystal J. Lee
(74) *Attorney, Agent, or Firm* — Andrus Intellectual Property Law, LLP

(57) ABSTRACT

A cement plug is for plugging an annular region between a first casing and a second casing in a well. A method includes: perforating the first casing to open a flow path to the annular region; providing a magnetorheological cementitious slurry; inducing a magnetic field for affecting the physical properties of the magnetorheological cementitious slurry and for defining a lower boundary for the cement plug; feeding the magnetorheological cementitious slurry into the annular region through a perforation in the first casing; and impeding the mobility of the magnetorheological cementitious slurry in the annular region by exposing it to the magnetic field such that the magnetorheological cementitious slurry may consolidate substantially at the lower boundary without the need for a base device in the annular region.

17 Claims, 11 Drawing Sheets

(51) Int. Cl.
*C09K 8/42* (2006.01)
*G01N 33/38* (2006.01)

(56) References Cited

U.S. PATENT DOCUMENTS

| | | | |
|---|---|---|---|
| 2015/0034311 A1* | 2/2015 | Tunget | E21B 47/005 |
| | | | 166/250.14 |
| 2015/0345250 A1 | 12/2015 | Murphree et al. | |
| 2016/0010424 A1* | 1/2016 | van Oort | E21B 33/13 |
| | | | 166/293 |
| 2017/0218748 A1* | 8/2017 | Ganssle | E21B 47/135 |
| 2017/0268312 A1* | 9/2017 | Haake | E21B 33/13 |
| 2020/0123894 A1* | 4/2020 | Ross | E21B 47/13 |

FOREIGN PATENT DOCUMENTS

| | | | | |
|---|---|---|---|---|
| WO | 2013169255 | 11/2013 | | |
| WO | WO-2013169255 A1 * | 11/2013 | | E21B 33/13 |
| WO | 2015094266 | 6/2015 | | |
| WO | WO-2015094266 A1 * | 6/2015 | | E21B 33/12 |

OTHER PUBLICATIONS

Written Opinion of the International Searching Authority for PCT/NO2018/050035, dated May 4, 2018.
Norwegian Search Report for NO20170944, dated Oct. 6, 2017.
Norwegian Search Report for NO20170196, dated Jun. 22, 2017.

* cited by examiner

METHOD OF ESTABLISHING A CEMENT PLUG IN AN ANNULAR REGION BETWEEN A FIRST AND A SECOND CASING

CROSS-REFERENCE TO RELATED APPLICATIONS

This application is the U.S. national stage application of International Application PCT/NO2018/050035, filed Feb. 8, 2018, which international application was published on Aug. 16, 2018, as International Publication WO 2018/147745 in the English language. The International Application claims priority of Norwegian Patent Application Nos. 20170196, filed Feb. 8, 2017 and 20170944, filed Jun. 9, 2017. The international application and Norwegian applications are all incorporated herein by reference, in entirety.

FIELD

The present disclosure relates to a method of establishing a cement plug in an annular region between a first and a second casing. The disclosure further relates to a cement plug formed from a magnetorheological slurry, a well comprising the cement plug, and a system for establishing a cement plug in an annular region between a first casing and a second casing. There is also disclosed method of establishing a resin-based plug, in particular a magnetorheological resin-based plug, in a wellbore. The disclosure further relates to a resin-based plug formed from a magnetorheological resin-based slurry composition, a well comprising the resin-based plug, and a system for establishing a resin-based plug in a well bore.

BACKGROUND

Plugging hydrocarbon wellbores is a very common activity, performed for a multitude of purposes. One common purpose for plugging is for establishing a permanent downhole barrier to prevent water or hydrocarbon flow from the wellbore. Such a plug is generally known as an abandonment plug, usually including cement.

When setting a cement plug, it is required that the plug comprises a portion of "good cement". This is particularly true for abandonment plugs, where, according to oil & gas industry guidelines, it is required for the plug to have a significant length of good cement. "Good cement" implies that a plug has an effective bond with a surrounding casing and/or tubing and/or formation with no cracks, channelling or slumping, and that it has reached its designed compressive strength.

There are several problems related to current cementing techniques, making it difficult to satisfy the requirements. This leads to a practice where cement plugs are set that are typically 150 meters long, in the hope that the plugs will comprise the required length of good cement.

Typically, a fluid column is used to form a base for a cement plug. This, however, may be problematic. If the fluid column is not perfectly static, cement may be influenced by fluid losses or inflow while setting. As cement has a higher density than most fluids typically present in a well, it will tend to swap out with lighter fluids, causing contamination, channelling and movement. Furthermore, if the fluid is partly depleted from the wellbore or the fluid base suffered from reduced density due to barite sag over a well lifetime, it may not be fit to form the necessary base. These, and other problems, may cause issues such as: the cement plug being contaminated by wellbore fluids; the top of cement not being where expected; cement partially or completely entering loss zones in a formation; and failure to achieve an acceptable verification.

When setting a cement plug for obstructing a passage inside a casing, a mechanical plug can be set as a base. For abandonment plugs, however, it is often necessary for the plug to not only obstruct the passage inside a first casing, but also to obstruct the passage in an annular region between a second casing and a first, smaller diameter casing placed inside the second casing. Forming a base for cement slurry in an annular region between two sizes of casing may be problematic, as there is no natural physical access to the annular region.

Three methods are commonly used to deal with the lack of natural physical access to the annulus:

One method is to cut and pull a portion of casing. A tool is run down into the wellbore to cut out a piece of the first casing to remove the physical barrier to the annular region. The piece of casing is then pulled out of the wellbore. This method is time-consuming and costly, and comes with several risks. One risk is that the piece of casing may become stuck in the wellbore. Another risk is that the casing may be corroded, which may cause it to break into smaller pieces falling off into the wellbore during removal. This may cause a need to fish out several smaller pieces, which can cause major delays. Furthermore, the casing may have been contaminated with naturally occurring radioactive material downhole, making the casing a health and environmental hazard.

The second commonly used method is section milling, which involves running a milling device into the wellbore and cutting/milling away some of the casing. Then cementing is performed in the milled section. This method generates a lot of metal cuttings and debris, which can cause issues in the wellbore and for surface equipment, such as metal strips forming blockages as they tangle together.

The third method is to perforate the casing to gain access to the annulus and inject cement. This method generally injects a cleaning fluid to remove any debris before injecting cement. By monitoring fluid levels, it can be determined if cement has been successfully injected into the annulus, but there is no method to determine where the cement has been placed. This leads to annular cement jobs often not having circumferential bonds or having significant contaminations and/or slumping problems.

Common for the three methods discussed above is that they are time-consuming and that they require specialised equipment and a full drilling unit.

SUMMARY

The disclosure has for its object to remedy or to reduce at least one of the drawbacks of the prior art, or at least provide a useful alternative to prior art.

The object is achieved through features, which are specified in the description below and in the claims that follow.

The disclosure relates to a method of establishing a cement plug in an annular region between a first and a second casing.

The disclosure is defined by the independent patent claims. The dependent claims define advantageous embodiments of the disclosure.

In a first aspect, the disclosure more specifically relates to a method of establishing a cement plug in an annular region between a first casing and a second casing in a well, wherein the method comprises the steps of:

perforating the first casing to open a flow path to the annular region between the first casing and the second casing;

providing a magnetorheological cementitious slurry;

inducing a magnetic field for affecting the physical properties of the cementitious slurry and for defining a lower boundary for the annular region;

feeding the cementitious slurry into the annular region through a perforation in the first casing; and impeding the mobility of the magnetorheological cementitious slurry in the annular region by exposing it to the magnetic field such that the magnetorheological cementitious slurry may consolidate substantially at the lower boundary without the need for a base device in the annular region.

The plug being established is a plug in the annular region between the first and the second casing. The plug may comprise an annular part and a central part, wherein the two parts may be connected through perforations in the first casing, wherein the annular part is located in the annular region between the first casing and the second casing, and wherein the central part is located within the first casing. Herein, a "cement plug" refers to a plug having at least an annular part, but it may also have a central part.

The annular part of the plug and the central part of the plug may have substantially corresponding lengths, they may be placed at substantially corresponding depths, they may have different lengths and/or they may be placed at different depths.

Note that it is to be understood that the term "casing" herein may cover any relevant tubular structure installed in a well, ranging from a conductor casing to a production tubing. Furthermore, it is to be understood that the term magnetorheological cementitious slurry may cover any cementitious slurry capable of having its physical properties affected by exposure to a magnetic field.

Note further that the word "perforating" herein refers to the act of making a hole in a casing. In the oil and gas industry, perforating often refers to blowing holes in a casing by use of an explosive charge. Herein, perforating may refer to any means of making a hole in a casing by any means suitable for the purpose, such as by piercing, drilling or by use of an explosive charge. Similarly, perforations refers to holes made in a casing by the act of perforating, and perforating means may be any means suitable for the act of perforating. The hole will typically be a hole big enough to form a flow path for a cementitious slurry, but not of the magnitude as holes in a casing typically resulting from a milling or cutting method.

A magnetorheological cementitious slurry is known to a person skilled in the art. Among the properties that may be altered by exposing a magnetorheological cementitious slurry to a magnetic field is the rheology, the viscosity and the shear strength. This effect is taken advantage of by the disclosure, to solve the problem of the lack of an efficient base for a plug in an annulus between two casings: By affecting the physical properties of the magnetorheological cementitious slurry in the annular region between the first casing and the second casing, the magnetorheological cementitious slurry is impeded from moving or slumping downwards from the region in which it is to form a plug. Thus, the magnetic field may define a lower boundary in the annular region for the cementitious slurry.

The magnetorheological cementitious slurry may comprise any type of particle for providing the magnetorheological properties, such as, but not limited to, carbonyl iron powder, electrolytic iron powder, hydrogen reduced iron powder and/or iron oxide powder.

The magnetorheological cementitious slurry may comprise cement slurry additives, such as, but not limited to:

an accelerator for reducing cement setting time;

a dispersant for decreasing the viscosity of a fluid;

a fluid loss control agent for controlling loss of a fluid through filtration;

an extender for decreasing the density of a fluid or for increasing the yield point of a fluid;

a retarder for increasing cement setting time; and/or a surfactant for limiting flocculation.

The magnetorheological cementitious slurry may be fed into the annular region by use of gravity and/or by use of applied injection pressure. Using applied injection pressure may be particularly advantageous as it may help in ensuring that voids are filled properly, thus removing or at least limiting contaminations in the cement. The magnetorheological cementitious slurry may be fed from cement providing means, such as a dump bailer, a coiled tubing, a drill pipe, or any other type of cement providing means suitable for the purpose. Feeding the cement via coiled tubing or using a cement reservoir, such as a dump bailer, suspended via wireline, allows for the use of a light intervention vessel rather than a drilling rig or drilling vessel. Using a light intervention vessel is significantly less expensive than a drilling rig or drilling vessel.

The method may further comprise the step of:

setting a base device in the first casing.

The base device in the first casing may be a bridge plug or an inflatable/swellable packer, or any other plug or device suitable for forming a physical base for a cementitious slurry. The base device may form a solid base for the cementitious slurry to build from to form a cement column to form a cement plug. The base device may typically be a bridge plug placed at a predetermined depth, to form a lower boundary for the cement plug in the first casing, prior to the step of feeding the cementitious slurry into the annular region.

The method may further comprise the step of:

installing a first magnetic field inducing member in the well at a predetermined depth.

The magnetic field inducing means may induce a magnetic field for altering physical properties of the magnetorheological cementitious slurry. It is advantageous to have a magnetic field inducing means installed in the well at a predetermined depth to define the depth for the base for the cement plug. The first magnetic field inducing member may be set prior to a base device, if present, and/or at a greater depth than the base device. It may also be set above the base device. The first magnetic field inducing member may be set just slightly above or slightly below the base device, or it may be comprised by the base device. Typically, the first magnetic field inducing member may be installed by anchoring it to the first casing, at a predetermined depth chosen to set a lower boundary for the cement plug in the annular region. The first magnetic field inducing member may typically be installed prior to the step of feeding the cementitious slurry into the annular region, and if a base device is set, the first magnetic field inducing member may typically be installed prior to the step of setting the base device.

The method may further comprise the step of:

installing a second magnetic field inducing member in the well at a predetermined depth, a distance above the first magnetic field inducing member.

Having a second magnetic field inducing member placed a distance above the first magnetic field inducing member may be beneficial, as it may induce a magnetic field to alter the physical properties of the magnetorheological cementitious slurry such that an upper boundary may be formed.

The upper boundary may work in a similar manner as the lower base for the cement plug: The magnetic field induced may alter the physical properties of the magnetorheological cementitious slurry to make it less mobile, thus impeding the cementitious slurry from moving upwards beyond the upper boundary, even if pressurized to a degree. Thus, applied injection pressure may be used to ensure that voids are filled with cement and that contaminations are removed, and to ensure a higher quality cement plug, without the magnetorheological cementitious slurry extending significantly beyond the base or the upper boundary. The first and second magnetic field inducing means may form the lower and upper boundaries, respectively, of the same cement plug.

The magnetic field inducing means, comprising the first magnetic field inducing member and the second magnetic field inducing member, may comprise an electro magnet powered by means of a power source connected to the magnetic field inducing means. The magnetic field inducing means may comprise an energise-to-hold magnet and/or an energise-to-release magnet. The power source may be any power source suitable for the purpose, such as a battery or a generator. The power source may be placed downhole or on the surface. The power source may be placed in the well below the first magnetic field inducing member, between the first magnetic field inducing member and the second magnetic field inducing member, above the second magnetic field inducing member, on a rig or a vessel, or elsewhere outside of the well. The magnetic field inducing means may comprise a permanent magnet. The magnetic field inducing means may comprise any other sort of magnetic field inducing means suitable for the purpose. Typically, the first magnetic field inducing member may be an electromagnet powered by a downhole battery connected to the electromagnet, the electromagnet being placed just below the base device at a predetermined depth in which it is desirable to form the base for the plug in the annular region between the first casing and the second casing. The downhole battery may typically be placed near the first magnetic field inducing member, below the base device. The second magnetic field inducing member may typically be powered by a power source located outside of the well or placed in the well above the second magnetic field inducing member.

A magnetic field may be induced via an electrical cable running to the surface, via application of an electromagnetic field to a casing string, such as the first casing or the second casing, or via a tubular string located in the wellbore, such as a drill pipe, a tubing, a coiled tubing, a workover string, a work string, a completion string, or any other type of tubular string suitable for the purpose. The magnetic field inducing means may thus further comprise any one or more of an electrical cable, a casing string or a tubular string.

The second magnetic field inducing member may typically be installed prior to the step of feeding the cementitious slurry into the annular region.

Furthermore, the method may comprise the step of:
stopping the magnetic field inducing means from inducing a magnetic field.

It may be beneficial to turn off the magnetic field inducing means if they are power consuming, for preserving energy. This may typically be done when the magnetorheological cementitious slurry has formed into a cement plug that has reached an acceptable compressive strength. Furthermore, it may be beneficial to have the magnetic field inducing means not induce a magnetic field when it is being run into the wellbore, to keep it from sticking to metal equipment.

The method may further comprise the step of:
testing the quality of the cement plug when the magnetorheological cementitious slurry has hardened and formed a cement plug.

A test of the quality of the plug may be performed, to ensure that the plug satisfies applicable abandonment guidelines. There are a number of ways to test the quality:

Volumetric verification: The volume of magnetorheological cementitious slurry placed into the annular region may be measured and compared to the theoretical volume of the annular region.

Pressure response: If the magnetorheological cementitious slurry is introduced to the annular region under pressure, the injection pressure may be monitored. As the annular region is filled, the injection pressure response will then change. A significant injection pressure increase would indicate that the entire annular region between the upper boundary and the base has been filled with cementitious slurry.

Ultrasonic logging: An ultrasonic bond log may be performed from above to provide an indication of cement bond quality in the annular region once the magnetorheological cementitious slurry has hardened and formed a cement plug.

Resistive or inductive logging: Due to the magnetic properties of the cement, an inductive or resistive log may be performed from above to provide an indication of cement bond quality in the annular region once the magnetorheological cementitious slurry has hardened.

Alternative logging techniques which take advantage of the magnetic properties of the cement may be employed, for example magnetic flux imaging tools.

Pressure testing from below: A pressure test may be performed from below in order to provide an indication of cement bond quality. A method for performing a pressure test from below is described in patent application NO20161939, which is hereby included by reference.

The logging methods proposed above, to check the quality of a cement plug, may be performed laterally and/or vertically. Typically, in the prior art, logging tools are lowered into a predetermined position inside a casing to create an image of a cement plug in an annular region on an outside of the casing. It is proposed herein that logging tools may be used to perform vertical, top down or bottom up, logging of a cement plug, by lowering the logging tool to a plug set within a casing.

The purpose of a plug is typically to form a barrier to prevent flow of hydrocarbons or other wellbore fluids, such as water and gas, from below the plug. Pressure tests, however, are typically performed from above, by building up an overpressure above the plug relative to below the plug. Above and below in this context should be construed as closest to surface and closest to the bottom of the well, respectively. A successful pressure test from above can only verify that a plug is able to withstand overpressure from above, and cannot confirm that the plug can successfully act as a barrier against overpressure from below, i.e. in the natural direction of fluid flow. It is therefore advantageous to perform a pressure test from below, as that will test the ability of the plug to withstand a pressure build up from below, which is what the plug is put in place to withstand. Certain applicable regulatory standards state that a well barrier should be tested from the direction of potential flow whenever possible.

The method of performing a pressure test from below may comprise the following steps:

installing a system for performing a pressure test from below in the well;

creating a confined testing space directly below the cement plug by use of a barrier element, wherein the barrier element forms a lower end of the confined testing space;

pressurizing fluid from a fluid reservoir and releasing said pressurized fluid into the confined testing space by means of a pressurizing member;

measuring pressure in relation to the confined testing space by means of the pressure sensor; and transmitting pressure data from the pressure sensor to a pressure data receiver.

The confined testing space is created directly below the cement plug, prior to the installation of the cement plug. The system for performing a pressure test from below may be installed at least partly within the confined testing space and partly in direct and/or indirect communication with items placed within the confined testing space. In one embodiment the fluid reservoir, a power source, the pressure sensor, the pressurizing member and data transmission means may be placed within the confined testing space, the barrier element may form the lower end of the confined testing space, while a data receiver is placed uphole from the confined testing space and the cement plug. In another embodiment, the fluid reservoir and the pressurizing means may be placed outside of the confined testing space, with the system having a conduit that extends from the fluid reservoir into the confined testing space so that fluid may be transported through the conduit from the fluid reservoir into the confined testing space. The data transmission means may be transmission means for transmitting data wirelessly.

The method may comprise the step of transferring data wirelessly by use of the data transmission means. The method may comprise the step of recording pressure as a function of time, and storing multiple pressure/time value pairs.

Resistive and/or inductive logging and/or ultrasonic logging are beneficial imaging tools that may show the bond between cement and steel casing, micro cracks and micro annulus. Data from such logging tools may be used to analyse a cement plug, to see whether the quality of the cement plug is acceptable.

Any one of or any combination of the above-mentioned testing methods may be performed as part of the method according to the disclosure. Furthermore, other methods of testing may be performed as part of the method according to the disclosure.

The method may further comprise the step of:

performing a logging and/or imaging operation for gathering information regarding pipe-to-cement bond quality and downhole pipe condition as a preparation to a plug-setting job.

Furthermore, the method may comprise the step of:

performing a lateral logging of a cement plug set in the annular region between the first casing and the second casing.

The method may further comprise the step of:

setting a cement plug inside the first casing after having performed a lateral logging of a cement plug in the annular region.

The method of performing a lateral logging may be performed using known techniques for logging, e.g. using ultrasonic logging tools, for verifying cement quality. The method may comprise the step of lowering an ultrasonic logging tool into the first casing to a predetermined depth corresponding to the depth of the annular plug.

In a second aspect, the disclosure relates to a cement plug, comprising an annular part, wherein the cement plug is formed from the magnetorheological cementitious slurry, wherein the cement plug substantially fills an annular region between a first casing and a second casing. The annular region between the first casing and the second casing may be restricted downwardly by a lower boundary defined by a first magnetic field, wherein the first magnetic field may be induced by a first magnetic field inducing member. The annular region may be restricted upwardly by an upper boundary defined by a second magnetic field, wherein the second magnetic field may be induced by a second magnetic field inducing member. The first and second magnetic field inducing means may form the lower and upper boundaries, respectively, of the same cement plug.

The cement plug may further comprise a central part substantially filling a region of the first casing, an inner region, such that the plug comprises a central part and an annular part. The inner region may be restricted upwardly by an upper boundary and downwardly by a lower boundary. The lower boundaries for the central part and the annular part may be substantially corresponding in depth in the well or they may be set at different depths. Likewise, the upper boundaries for the two parts may be substantially corresponding in depth or they may be set at different depths. The length of the annular part and the central part may be substantially equal, or it may be different.

The cement plug may comprise a length of the first casing having its outer side substantially covered by the cement of the annular part of the cement plug, wherein the length of the first casing is substantially intact, apart from one or more perforations. The length of the first casing may substantially correspond in length to the annular part of the cement plug. The length of the first casing may further be completely or partly covered on its inner side by the cement of a central part of the cement plug.

The cement plug may be the result of the method according to the first aspect of the disclosure. As described with regards to the method, the cement plug may be advantageous as the use of a magnetorheological cementitious slurry may ensure a higher quality cement.

In a third aspect, the disclosure relates to a well comprising the cement plug.

It may be advantageous for a well having a cement plug set by use of the method according to the first aspect of the disclosure, as such a plug may be of a higher quality than a plug formed by a conventional cementing method. A cement abandonment plug set by use of this method may provide a better, more reliable barrier, than a typical cement abandonment plug.

The well may be any well in which a cement plug may be used, wherein the well comprises at least two casings.

The well may further comprise a perforated first casing along at least a part of the length of the cement plug, wherein the first casing along the length of the cement plug is otherwise substantially intact.

Often, when setting a cement plug, a part of a first casing is removed. This is time consuming, difficult, expensive and potentially hazardous, as the casing may be contaminated by naturally occurring radioactive material downhole. It is therefore highly beneficial to leave the first casing substantially intact, and to not fish a piece of the casing out of the well when setting the cement plug.

In a fourth aspect, the disclosure relates to a system for establishing a plug in an annular region between a first casing and a second casing, wherein the system comprises the first magnetic field inducing member for inducing a magnetic field, the magnetorheological cement slurry for forming the plug, the cement providing means, and perforating means for perforating the first casing.

The perforating means may be any means known for a person skilled in the art suitable for the purpose of perforating a casing in a well, such as drilling means, piercing means or means for perforating by use of an explosive charge.

The system for plugging a well is advantageous as it allows for setting a plug according to the method according to the first aspect of the disclosure. The benefits of using said methods have been discussed previously in this text.

Furthermore, the system for plugging a well may comprise a second magnetic field inducing member for inducing a second magnetic field.

The second magnetic field inducing member is advantageous as it allows for setting an upper boundary for the cement plug, and allows for added injection pressure when injecting cement. The added injection pressure may aid in removing contaminations in the cement or filling small voids, thus improving the quality of the cement plug.

Furthermore, the system for plugging a well may comprise testing means for testing the quality of the cement plug after it has hardened.

The testing means may be any type of testing means for performing a pressure test, an imaging test or any other test suitable for providing information regarding the quality of the cement plug.

The testing means may be ultrasonic logging tools, resistive logging tools, inductive logging tools, means for performing a pressure test from above, or means for performing a pressure test from below.

The means for performing a pressure test from below may comprise:
- a barrier for setting a barrier in the well, below the plug, to create a confined testing space between the barrier and the plug;
- a fluid reservoir for storing a fluid;
- a pressurizing member for pressurizing the fluid from said fluid reservoir and for transferring the pressurized fluid into the confined testing space;
- a pressure sensor for measuring pressure in relation to said confined testing space; and
- a pressure data receiver for receiving pressure data from said pressure sensor.

The pressure data receiver may be provided above said first barrier or it may be provided below said first barrier. The pressure data receiver may be adapted to receive pressure data directly from said pressure sensor, or said pressure data receiver may be adapted to receive pressure data from a storage unit adapted to receive and store pressure data from said pressure sensor The testing means may comprise a data storing means and a data transferring means, a power source, and other means that are obvious for a person skilled in the art.

Testing means is advantageous to the system, as testing the quality of the plug after it has been set is an important safety measure and in many cases a requirement.

The disclosure further relates to a method of establishing a resin-based plug, and in particular a magnetorheological resin-based plug, in a well bore.

The disclosure is defined by the independent patent claims. The dependent claims define advantageous embodiments of the disclosure.

In a fifth aspect, the disclosure more specifically relates to a magnetorheological resin-based slurry composition for establishing a plug in a wellbore comprising at least one natural and/or artificial resin; and ferrous particles.

Use of at least one resin within the slurry composition has been found to provide a resin-based plug with improved properties compared to standard oilfield barriers, such as for example cement based barriers or plugs. These improved properties include, but are not limited to: compressive strength, tensile strength, permeability, flexural strength, rupture elongation, etc. It has also been found that the setting times for the resin-based slurry compositions of the present disclosure can be accurately controlled to allow a wellbore to have effective well integrity over a very short time period when compared to conventional wellbore sealing compositions.

Another advantage of using a resin-based slurry is that the slurry may also serve to thermally destroy, or melt, control line cables which are installed as part of a completion string. This may allow for the completions string to remain in the hole during well abandonments rather than recovering to surface.

The magnetorheological resin-based slurry composition may comprise any type of ferrous particles for providing the magnetorheological properties, such as, but not limited to carbonyl iron powder, electrolytic iron powder, hydrogen reduced iron powder, and iron oxide powder, and any combination thereof.

The magnetorheological resin-based slurry composition may comprise microscale sized particles.

The magnetorheological resin-based slurry composition may further comprise one or more slurry additives, such as, but not limited to:
- an accelerator for reducing setting time;
- a dispersant for decreasing the viscosity of a fluid;
- a fluid loss control agent for controlling loss of a fluid through filtration;
- an extender for decreasing the density of a fluid or for increasing the yield point of a fluid;
- a retarder for increasing setting time; and/or
- a surfactant for limiting flocculation.

The magnetorheological resin-based slurry composition may comprise one or more additional wellbore barrier mediums such as for example, but not to be limited to, cement, resin, sand, thermite, magnetorheological blended cement, natural barriers such as shale or salt, or any combination thereof.

Among the properties that may be altered by exposing the magnetorheological resin-based slurry composition to a magnetic field are: the rheology, the viscosity and the shear strength of the composition. For example, the viscosity of the magnetorheological resin-based slurry composition may increase, and therefore movement of the resin-based slurry composition within the wellbore may be impeded, as the applied magnetic field increases. As such, the location of the slurry composition within the wellbore can be very accurately controlled and maintained effectively by exposure to a magnetic field during formation of the resin-based plug without the need for an additional base device being present within the wellbore. A circulating/alternating magnetic field may also be used to create radial flow the resin-based slurry composition, which may be beneficial for improved displacement and this Exposure to a magnetic field may also increase the rheology of the magnetorheological resin-based slurry composition and as such may offer one or more of the following benefits:

reducing fluid 'swap-out' effects due to gravitational migration if the slurry composition has a higher density than surrounding fluids.

reducing fluid loss to formation.

reducing the effects of 'loss of hydrostatic head' as the slurry composition hardens.

the ability to 'suspend' the slurry composition in an annular space between two or more casing strings.

enabling the slurry composition to effectively solidify at a predetermined location on demand under the application of magnetic field.

inhibits the flow of gasses or fluids past the slurry composition during the period between application of the magnetic field and the time at which the slurry composition has developed adequate compressive strength to form the plug.

reducing likelihood of barrier channelling effects.

reducing likelihood of barrier contamination.

The effects of exposure to a magnetic field on the viscosity, rheology and shear strength of the resin-based slurry composition are taken advantage of by the disclosure, to solve the problem of providing a homogenous and continuous hydraulic plug with improved physical properties at an accurately controlled predetermined location within a wellbore while providing a high-quality bond with enhanced well integrity.

In a sixth aspect, the disclosure more specifically relates to a method for establishing a hydraulic plug in a well bore, comprising the steps of:

providing a magnetorheological resin-based slurry composition to a wellbore;

providing at least a first magnetic field inducing member; and operating the at least a first magnetic field inducing member so as to expose the magnetoreheological resin-based slurry composition to a magnetic field sufficient to cause consolidation of the magnetorheological resin-based slurry composition to provide a resin-based plug at a predetermined location within the wellbore.

The magnetorheological resin-based slurry composition of the disclosure may be provided to the well bore by any suitable methods such as for example one or more of the following:

pumping down inside the casing string;

pumping down into an annular region;

pumping through a tubular string such as provided by a drillpipe, coil tubing;

conveying into the well on a dump bailer or similar on wireline or another non-fluid carrying cable.

The magnetorheological resin-based slurry composition may be fed into the well bore by use of gravity and/or by use of applied injection pressure. Using applied injection pressure may be particularly advantageous as it may help in ensuring that voids are filled properly, thus removing or at least limiting contaminations in the resin-based slurry composition. The magnetorheological resin-based slurry composition may be fed from any suitable resin providing means, such as a dump bailer, a coiled tubing, a drill pipe. Feeding the slurry composition via coiled tubing or using a reservoir, such as a dump bailer, suspended via wireline, allows for the use of a light intervention vessel rather than a drilling rig or drilling vessel. Using a light intervention vessel is significantly less expensive than a drilling rig or drilling vessel.

In one embodiment, an annular region is provided between a first casing and a second casing within a wellbore. The plug may be formed in the annular region located between the first and the second casing.

The method for establishing a hydraulic plug in a wellbore comprising a first and second casing defining an annular region may further comprise:

providing a flow path between a first casing and an annular region located between a first casing and a second casing; and feeding the magnetorheological resin-based slurry composition into the annular region via the flow path in the first casing.

The flow path may be provided via one or more of, but not limited to:

casing perforations section milling drilling holes cut & pull casing existing sliding sleeve, stage collar or any other method of existing casing conduits.

The method of the disclosure may therefore enable primary zonal isolation by pumping the magnetorheological resin-based slurry composition into the annular region between a casing and a well bore, or other casings or tubing strings during well construction and work-over.

Exposure to the magnetic field may continue for any suitable period of time in order to allow formation of a resin-based plug having adequate compressive strength to support the well bore conditions.

The method may further comprise the step of:

setting a base device in the well bore.

The base device may be a bridge plug or an inflatable/swellable packer, or any other plug or device suitable for forming a physical base for the resin-based slurry composition. The base device may form a solid base for the resin-based slurry composition to build from to form a resin-based column to form a resin-based plug. The base device may typically be a bridge plug placed at a predetermined depth, to form a lower boundary for the resin-based plug, prior to the step of feeding the resin-based slurry composition into the well bore.

The method may further comprise the step of:

installing at least a first magnetic field inducing member in the well at a predetermined depth.

The at least first magnetic field inducing means may induce a magnetic field for altering physical properties of the magnetorheological resin-based slurry composition. It is advantageous to have a magnetic field inducing means installed in the well at a predetermined depth to define the depth for the base for the resin-based plug. The first magnetic field inducing member may be set prior to a base device, if present, and/or at a greater depth than the base device. It may also be set above the base device. The first magnetic field inducing member may be set just slightly above or slightly below the base device, or it may be comprised by the base device. In one embodiment, the first magnetic field inducing member may be installed by anchoring it to a first casing, at a predetermined depth chosen to set a lower boundary for the plug in the annular region. The first magnetic field inducing member may typically be installed prior to the step of feeding the slurry composition into the annular region, and if a base device is set, the first magnetic field inducing member may typically be installed prior to the step of setting the base device.

The method may further comprise the step of:

installing a second magnetic field inducing member in the well at a predetermined depth, a distance above the first magnetic field inducing member.

Having a second magnetic field inducing member placed a distance above the first magnetic field inducing member may be beneficial, as it may induce a magnetic field to alter the physical properties of the magnetorheological resin-based slurry composition such that an upper boundary may be formed. The first and second magnetic field inducing means may form the lower and upper boundaries, respectively, of the same resin-based plug. The upper boundary may work in a similar manner as the lower base device for the resin plug. The magnetic field induced may alter the physical properties of the magnetorheological resin-based slurry composition to make it less mobile, thus impeding the resin slurry from moving upwards beyond the upper boundary, even if pressurized to a degree. Thus, applied injection pressure may be used to ensure that voids are filled with resin and that contaminations are removed, and to ensure a higher quality resin plug, without the magnetorheological resin-based slurry composition extending significantly beyond the base or the upper boundary.

The magnetic field inducing means, comprising the at least first magnetic field inducing member, may comprise an electromagnet powered by means of a power source connected to the magnetic field inducing means. The magnetic field inducing means may comprise an energise-to-hold magnet and/or an energise-to-release magnet. The power source may be any power source suitable for the purpose, such as a battery or a generator. The power source may be placed downhole or on the surface. The power source may be placed in the well below a first magnetic field inducing member, between a first magnetic field inducing member and a second magnetic field inducing member, above a second magnetic field inducing member, on a rig or a vessel, or elsewhere outside of the well bore. The magnetic field inducing means may comprise a permanent magnet. The magnetic field inducing means may comprise any other sort of magnetic field inducing means suitable for the purpose. Typically, the first magnetic field inducing member may be an electromagnet powered by a downhole battery connected to the electromagnet, the electromagnet being placed just below a base device at a predetermined depth in which it is desirable to form the base for the plug. The downhole battery may typically be placed near a first magnetic field inducing member, below the base device. The second magnetic field inducing member may typically be powered by a power source located outside of the well or placed in the well above the second magnetic field inducing member.

A magnetic field may be induced via an electrical cable running to the surface, via application of an electromagnetic field to a casing string, such as the first casing or the second casing, or via a tubular string located in the wellbore, such as a drill pipe, a tubing, a coiled tubing, a workover string, a work string, a completion string, or any other type of tubular string suitable for the purpose. The magnetic field inducing means may thus further comprise any one or more of an electrical cable, a casing string or a tubular string.

The second magnetic field inducing member may typically be installed prior to the step of feeding the resin-based slurry composition into the well bore.

Furthermore, the method may comprise the step of:
stopping the magnetic field inducing means from inducing a magnetic field.

It may be beneficial to turn off the magnetic field inducing means if they are power consuming, for preserving energy. This may typically be done when the magnetorheological resin slurry has formed into a resin plug that has reached an acceptable compressive strength. Furthermore, it may be beneficial to have the magnetic field inducing means not induce a magnetic field when it is being run into the wellbore, to keep it from sticking to metal equipment.

The method may further comprise the step of:
testing the quality of the resin plug when the magnetorheological resin-based slurry composition has hardened and formed a resin-based plug.

A test of the quality of the resin-based plug may be performed, to ensure that the plug satisfies applicable abandonment guidelines. There are a number of ways to test the quality:

Volumetric verification: The volume of magnetorheological resin slurry placed into the annular region may be measured and compared to the theoretical volume of the annular region.

Pressure response: If the magnetorheological resin-based slurry composition is introduced under pressure to an annular region located between a first and second casing, the injection pressure may be monitored. As the annular region is filled, the injection pressure response will then change. A significant injection pressure increase would indicate that the entire annular region between the upper boundary and the base has been filled with resin slurry.

Ultrasonic logging: An ultrasonic bond log may be performed from above to provide an indication of resin bond quality in the annular region once the magnetorheological resin slurry has hardened and formed a resin plug.

Resistive or inductive logging: Due to the magnetic properties of the resin, an inductive or resistive log may be performed from above to provide an indication of cement bond quality in the annular region once the magnetorheological resin slurry has hardened.

Alternative logging techniques which take advantage of the magnetic properties of the cement may be employed, for example magnetic flux imaging tools Pressure testing from below: A pressure test may be performed from below in order to provide an indication of resin bond quality. A method for performing a pressure test from below is described in patent application NO20161939, which is hereby included by reference.

The logging methods proposed above, to check the quality of a plug, may be performed laterally and/or vertically.

The purpose of a plug is typically to form a barrier to prevent flow of hydrocarbons or other wellbore fluids, such as water and gas, from below the plug. Pressure tests, however, are typically performed from above, by building up an overpressure above the plug relative to below the plug. Above and below in this context should be construed as closest to surface and closest to the bottom of the well, respectively. A successful pressure test from above can only verify that a plug is able to withstand overpressure from above and cannot confirm that the plug can successfully act as a barrier against overpressure from below, i.e. in the natural direction of fluid flow. It is therefore advantageous to perform a pressure test from below, as that will test the ability of the plug to withstand a pressure build up from below, which is what the plug is put in place to withstand. Certain applicable regulatory standards state that a well barrier should be tested from the direction of potential flow whenever possible.

The method of performing a pressure test from below may comprise the following steps:
installing a system for performing a pressure test from below in the well;

creating a confined testing space directly below the resin plug by use of a barrier element, wherein the barrier element forms a lower end of the confined testing space;

pressurizing fluid from a fluid reservoir and releasing said pressurized fluid into the confined testing space by means of a pressurizing member;

measuring pressure in relation to the confined testing space by means of the pressure sensor; and transmitting pressure data from the pressure sensor to a pressure data receiver.

The confined testing space is created directly below the plug, prior to the installation of the plug. The system for performing a pressure test from below may be installed at least partly within the confined testing space and partly in direct and/or indirect communication with items placed within the confined testing space. In one embodiment the fluid reservoir, a power source, the pressure sensor, the pressurizing member and data transmission means may be placed within the confined testing space, the barrier element may form the lower end of the confined testing space, while a data receiver is placed uphole from the confined testing space and the plug. In another embodiment, the fluid reservoir and the pressurizing means may be placed outside of the confined testing space, with the system having a conduit that extends from the fluid reservoir into the confined testing space so that fluid may be transported through the conduit from the fluid reservoir into the confined testing space. The data transmission means may be transmission means for transmitting data wirelessly.

The method may comprise the step of transferring data wirelessly by use of the data transmission means. The method may comprise the step of recording pressure as a function of time, and storing multiple pressure/time value pairs.

Resistive and/or inductive logging and/or ultrasonic logging are beneficial imaging tools that may show the bond between cement and steel casing, micro cracks and micro annulus. Data from such logging tools may be used to analyse a cement plug, to see whether the quality of the cement plug is acceptable.

Any one of or any combination of the above-mentioned testing methods may be performed as part of the method according to the disclosure. Furthermore, other methods of testing may be performed as part of the method according to the disclosure.

The method may further comprise the step of:
performing a logging and/or imaging operation for gathering information regarding pipe-toplug bond quality and downhole pipe condition as a preparation to a plug-setting job.

Furthermore, the method may comprise the step of:
performing a lateral logging of a plug set in an annular region between the first casing and the second casing.

The method may further comprise the step of:
setting a plug inside a first casing after having performed a lateral logging of a plug in the annular region.

The method of performing a lateral logging may be performed using known techniques for logging, e.g. using ultrasonic logging tools, for verifying quality. The method may comprise the step of lowering an ultrasonic logging tool into the first casing to a predetermined depth corresponding to the depth of the annular plug.

In a seventh aspect, the disclosure relates to a resin plug formed from the magnetorheological resin-based slurry composition.

The resin-based plug may be located at any suitable predetermined location and may extend across any suitable surfaces within the well bore.

The plug may be the result of the method according to the sixth aspect of the disclosure.

In one embodiment, the resin plug may substantially fill an annular region between a first casing and a second casing.

In a further embodiment, the plug may comprise an annular part and a central part, wherein the two parts may be connected via a flow path extending between a first casing and the annular region, for example through perforations located in the first casing. The annular part of the plug may be located in the annular region between the first casing and the second casing, and the central part of the plug may be located within the first casing.

The term "plug" preferably refers to a plug having at least an annular part, but it may also have a central part. The plug may for example cover the casing string in which the plug is set, and the annular space(s) between that casing string and adjacent casing strings.

The annular part of the plug and the central part of the plug may have any suitable dimensions and may be located at any suitable location within the wellbore. For example, the annular part and the central part may have substantially corresponding lengths and placed at substantially corresponding depths within the wellbore. Alternatively, the annular part and the central part may have different lengths and/or may be placed at different depths within the wellbore.

Note that it is to be understood that the term "casing" herein may cover any relevant tubular structure installed in a well, ranging from a conductor casing to a production tubing.

Note further that the word perforating herein refers to the act of making a hole in a casing. In the oil and gas industry, perforating often refers to blowing holes in a casing by use of an explosive charge. Herein, perforating may refer to any means of making a hole in a casing by any means suitable for the purpose, such as by piercing, drilling or by use of an explosive charge. Similarly, perforations refers to holes made in a casing by the act of perforating, and perforating means may be any means suitable for the act of perforating. The hole will typically be a hole big enough to form a flow path for a resin, but not of the magnitude as holes in a casing typically resulting from a milling or cutting method.

In an eight aspect, the disclosure relates to a well comprising a magnetorheological resin-based plug.

It may be advantageous for a well having a magnetorheological resin-based plug set by use of the method according to the sixth aspect of the disclosure, as such a plug may be of a higher quality with improved physical properties than a plug formed by a conventional cementing method.

The well may be any well in which a resin plug may be used. In one embodiment, the well may comprise at least two casings. The well may further comprise a flow path extending through at least a part of the length of a first casing, wherein the first casing along the length of the plug is otherwise substantially intact.

Often, when setting a plug, a part of a first casing is removed. This is time consuming, difficult, expensive and potentially hazardous, as the casing may be contaminated by naturally occurring radioactive material downhole. It is therefore highly beneficial to leave the first casing substantially intact, and to not fish a piece of the casing out of the well when setting the plug.

In a ninth aspect, the disclosure relates to a system for establishing a plug in a well bore, wherein the system comprises at least a first magnetic field inducing member for inducing a magnetic field, and the magnetorheological resin-based slurry composition as herein described.

The system may further comprise a resin slurry providing means.

The system for plugging a well is advantageous as it allows for setting a plug according to the method according to the fifth of the disclosure. The benefits of using said methods have been discussed previously in this text.

Furthermore, the system for plugging a well may comprise a second magnetic field inducing member for inducing a second magnetic field.

The second magnetic field inducing member is advantageous as it allows for setting an upper boundary for the plug, and allows for added injection pressure when injecting the resin-based slurry composition. The added injection pressure may aid in removing contaminations or filling small voids, thus improving the quality of the plug. The first and second magnetic field inducing means may form the lower and upper boundaries, respectively, of the same resin-based plug.

Furthermore, the system for plugging a well may comprise testing means for testing the quality of the resin-based plug after it has hardened.

The testing means may be any type of testing means for performing a pressure test, an imaging test or any other test suitable for providing information regarding the quality of the plug. The testing means may be ultrasonic logging tools, resistive logging tools, inductive logging tools, means for performing a pressure test from above, or means for performing a pressure test from below.

The means for performing a pressure test from below may comprise:
  a barrier for setting a barrier in the well, below the plug, to create a confined testing space between the barrier and the plug;
  a fluid reservoir for storing a fluid;
  a pressurizing member for pressurizing the fluid from said fluid reservoir and for transferring the pressurized fluid into the confined testing space;
  a pressure sensor for measuring pressure in relation to said confined testing space; and
  a pressure data receiver for receiving pressure data from said pressure sensor.

The pressure data receiver may be provided above said first barrier or it may be provided below said first barrier. The pressure data receiver may be adapted to receive pressure data directly from said pressure sensor, or said pressure data receiver may be adapted to receive pressure data from a storage unit adapted to receive and store pressure data from said pressure sensor The testing means may comprise a data storing means and a data transferring means, a power source, and other means that are obvious for a person skilled in the art.

Testing means is advantageous to the system, as testing the quality of the plug after it has been set is an important safety measure and in many cases a requirement.

BRIEF DESCRIPTION OF THE DRAWINGS

In the following are described examples of possible application of the methods according the disclosure illustrated in the accompanying drawings, wherein.

DETAILED DESCRIPTION OF THE DRAWINGS

Figure 1:
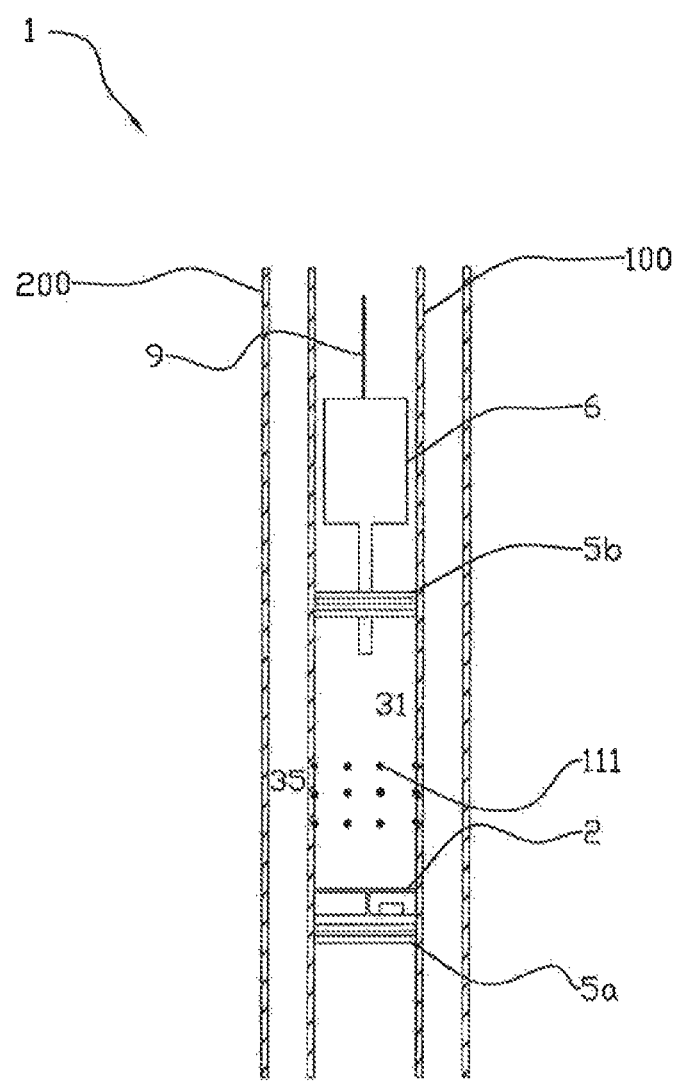
FIG. 1 shows parts of the system set up in a first casing prior to release of cement.

Note that the drawings are shown highly simplified and schematic and the various features therein are not necessarily drawn to scale. Identical reference numerals refer to identical or similar features in the drawings.

FIG. 1 shows some of the parts of an embodiment of the system 1 for establishing a plug in an annular region 35 between a first casing 100 and a second casing 200 according to disclosure. The first casing 100 is positioned inside the second casing 200.

The illustration shows an embodiment of the system 1 comprising a first electromagnet 5a, a bridge plug 2, a second electromagnet 5b, a cement providing means 6, in this embodiment shown comprising a dump bailer and a tube, for delivering cement through the second electromagnet 5b, into an inner region 31 inside the first casing 100 restricted upwardly by the second electromagnet 5b and downwardly by the bridge plug 2. The system 1 is connected to a not shown vessel by use of a wireline 9. The system further comprises perforating means, and a power source for each of the electromagnets 5a, 5b, not shown in the figure.

Furthermore, the figure shows that the first casing 100 has been perforated, so that a flow path through perforations 111 has been established from the inner region 31 to the annular region 35. The bridge plug 2, the second electromagnet 5b and the first casing 100 defines the boundaries of the inner region 31 within the first casing 100, which is in fluid communication with the annular region 35.

Figure 2:
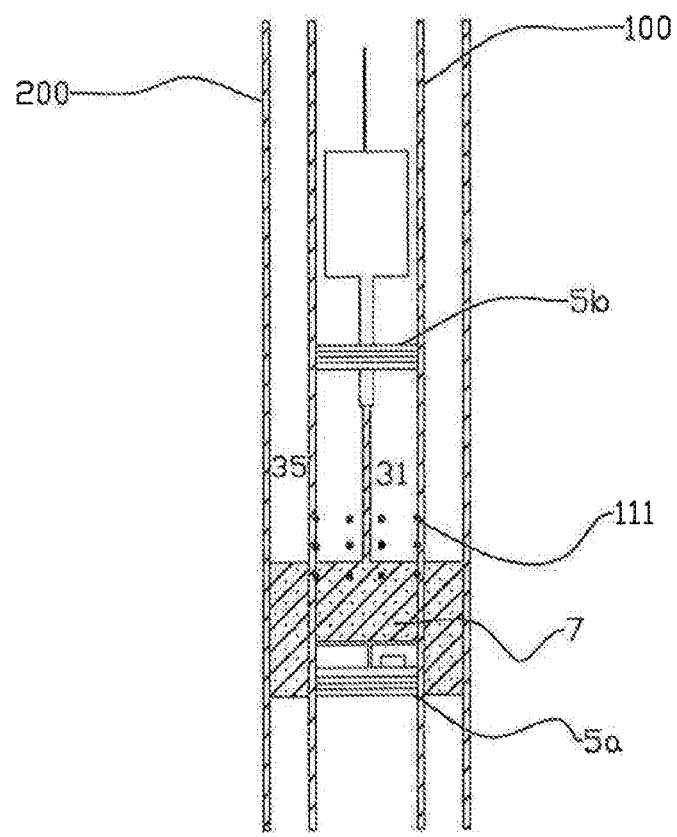
FIG. 2 shows magnetorheological cementitious slurry being released into an inner region and running out through perforations in the first casing into an annular region.

FIG. 2 shows magnetorheological cementitious slurry 7 being poured into the inner region 31. Furthermore, it shows that when the magnetorheological cementitious slurry 7 reaches the perforations 111, it flows into the annular region 35. The first electromagnet 5a is activated in this figure, inducing a first magnetic field, thus establishing a lower boundary for the magnetorheological cementitious slurry 7 in the annular region 35. The lower boundary keeps the magnetorheological cementitious slurry 7 from slumping downwards in the annular region 35. The magnetic field further defines the lower boundary for the annular region. The second electromagnet 5b is also activated, inducing a second magnetic field, thus forming the upper boundary for the magnetorheological cementitious slurry 7 in the annular region 35 and defining the upper boundary for the annular region 35. The upper boundary, the lower boundary, the second casing 200 and the first casing 100 defines the annular region 35.

Figure 3:
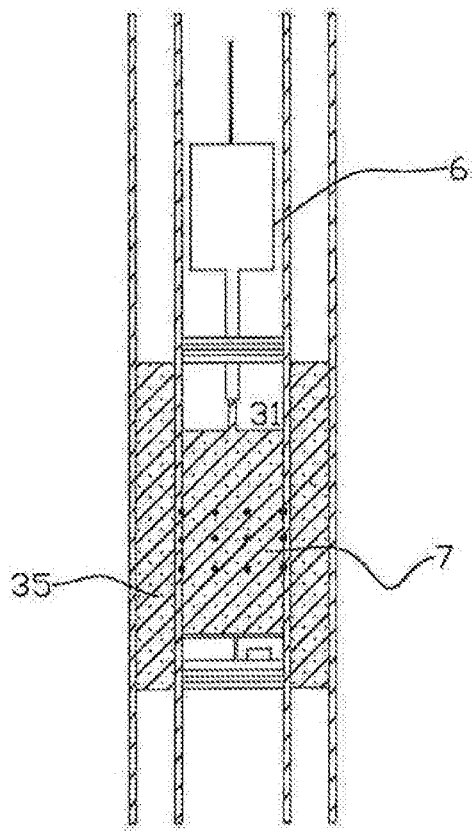
FIG. 3 shows the annular region being full of magnetorheological cementitious slurry while the inner region is still filling up.

FIG. 3 shows the magnetorheological cementitious slurry 7 as it is still being fed out from the cement providing means 6, at a point where the magnetorheological cementitious slurry 7 has reached the upper boundary of the annular region 35, but where there is a portion of the inner region 31 left to fill.

Figure 4:
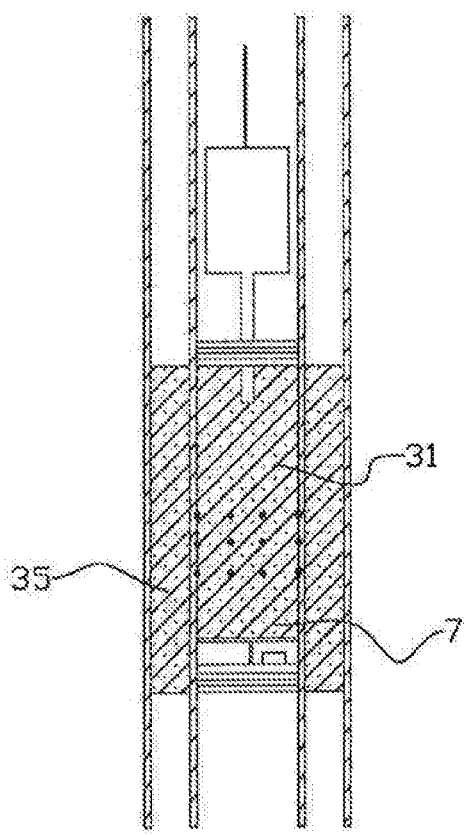
FIG. 4 shows both the annular region and the inner region being full of magnetorheological cementitious slurry.

In FIG. 4, both the inner region 31 and the annular region 35 have been substantially filled with magnetorheological slurry 7.

Figure 5:
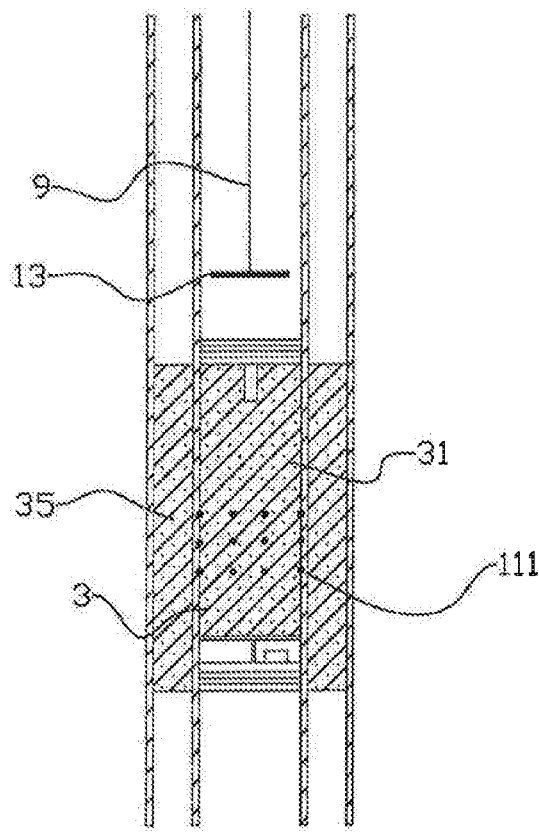
FIG. 5 shows ultrasonic logging of the cement plug after it has hardened.

FIG. 5 shows ultrasonic logging in process after the magnetorheological cementitious slurry 7 has formed into a cement plug 3. The cement plug 3 comprises two parts, connected through the perforations 111: an annular part of the plug and a central part of the plug, wherein the annular part is in the annular region 35 and the central part is in the inner region 31. An ultrasonic logging tool 13 is lowered in the wellbore to the vicinity of the cement plug 3 by use of a wireline 9 to perform the ultrasonic logging.

Figure 6:
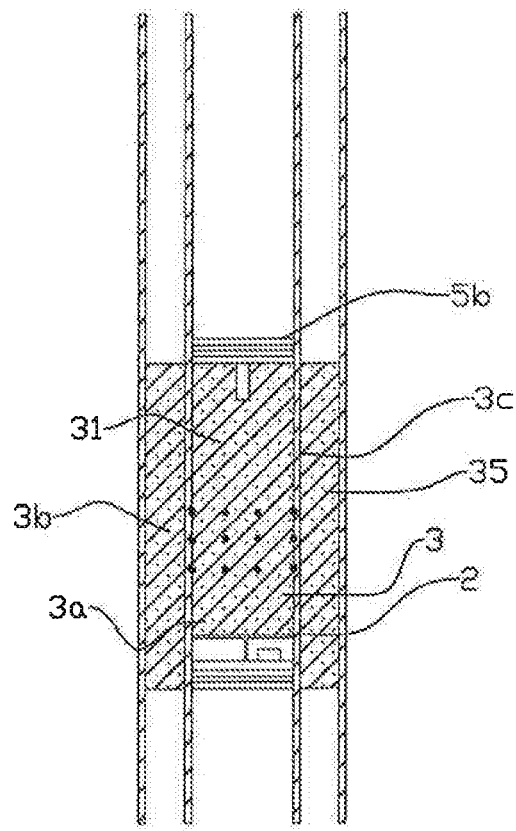
FIG. 6 shows the cement plug in place in the well after the method of establishing the plug has been completed.

FIG. 6 is a situational depiction of the wellbore after the method of establishing the cement plug 3 is completed. The cement plug 3 is in place in the annular region 35. In this embodiment, the cement plug 3 has both an annular part and a central part, wherein the annular part is of slightly greater length than the central part. The lower boundary in the annular region is slightly deeper in the wellbore than the bridge plug 2, while the upper boundary for the annular region 35 is substantially on line with the second electromagnet 5b that acts as an upper delimitation for the inner region 31.

The cement plug 3 shown in FIG. 6 comprises an annular part 3a, a central part 3b, and a length 3c of the first casing 100 substantially intact apart from perforations 111.

Figure 7:
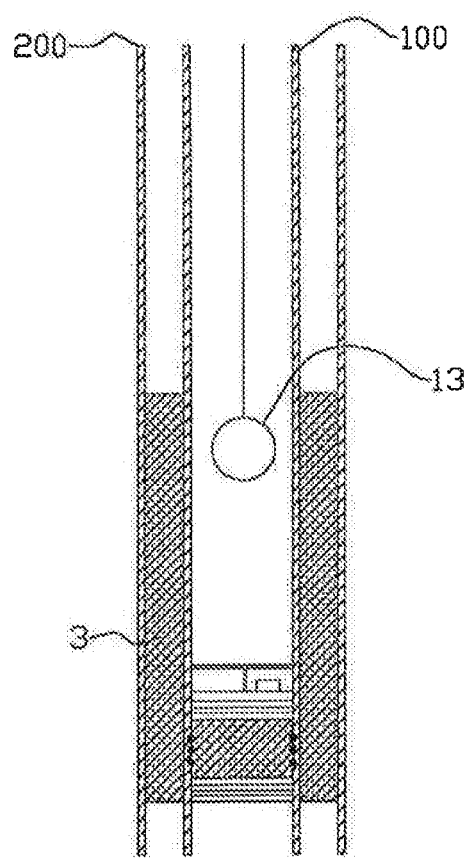
FIG. 7 shows a step of performing a lateral ultrasonic logging of an annular cement plug.

FIG. 7 shows a step of performing a lateral logging to verify the quality of a cement plug 3 set in an annulus between a first casing 100 and a second casing 200 by use of an ultrasonic logging tool 13. This may be done to verify the quality of the annular plug 3 prior to setting a central plug inside the first casing 100.

Figure 8:
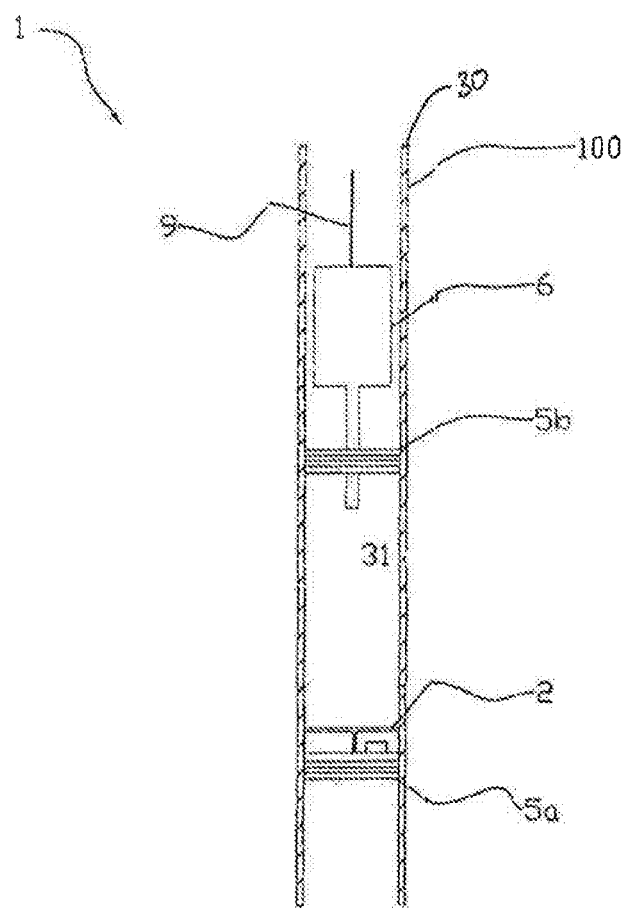
FIG. 8 shows one embodiment of the system of the present disclosure within a wellbore prior to release of a magnetorheological resin-based slurry composition.

FIG. 8 shows some of the parts of an embodiment of the system 1 for establishing a resin-based plug in a well bore 31. The system 1 comprises a first electromagnet 5a, a bridge plug 2, a second electromagnet 5b, a magnetorheological resin-based slurry composition providing means 6, in this embodiment shown comprising a dump bailer and a tube, for delivering a magnetorheological resin-based slurry composition through the second electromagnet 5b, into the wellbore 30 restricted upwardly by the second electromagnet 5b and downwardly by the bridge plug 2. The slurry composition may be delivered by injection under pressure. The system 1 is connected to a not shown vessel by use of a wireline 9. The system further comprises a power source for each of the electromagnets 5a, 5b, not shown in the figure.

The inner walls of the wellbore 30, the bridge plug 2, the first electromagnet 5a, and the second electromagnet 5b define the boundaries of the cavity 31 within which the plug is to be formed within the wellbore 31. It is however to be understood that in some embodiments the system may not comprise a bridge plug 2 and that the lower limit of the plug formed from the slurry composition may be controlled by application of a magnetic field from a first electromagnet 5a alone.

Figure 9:
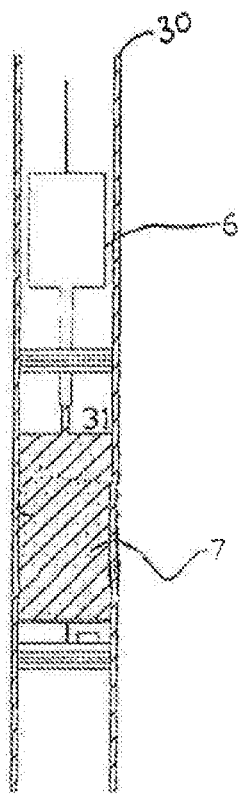
FIG. 9 shows the system of FIG. 1 during introduction of a magnetorheological resin-based slurry composition into the wellbore.

FIG. 9 shows magnetorheological resin-based slurry composition 7 being poured into the cavity 31. The first electromagnet 5a is activated in this figure, inducing a first magnetic field, thus establishing a lower boundary for the magnetorheological resin-based slurry composition 7. The second electromagnet 5b is also activated, inducing a second magnetic field, thus forming the upper boundary for the magnetorheological resin-based slurry composition 7 in cavity 31. The magnetorheological resin-based slurry composition 7 is fed into cavity 31 until it has been substantially filled. During operation of the electromagnets 5a and 5b, the magnetic field reduces the viscosity of the slurry enabling formation of the plug.

Figure 10:
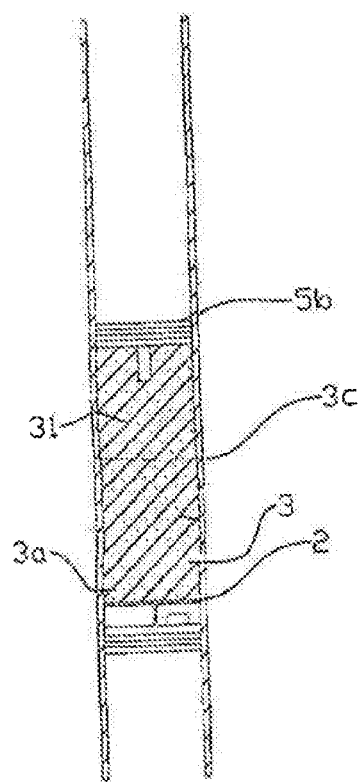
FIG. 10 shows the resin-based plug in place in the wellbore after the method of establishing the plug has been completed.

FIG. 10 is a situational depiction of the wellbore after the method of establishing the resin-based plug 3 is completed. The plug 3 is in place in the cavity 31. In this embodiment, the plug 3 extends across the wellbore 30. The plug 3 is a homogenous mass and provides a continuous hydraulic seal with an improved bond to provide enhanced well integrity.

Figure 11:
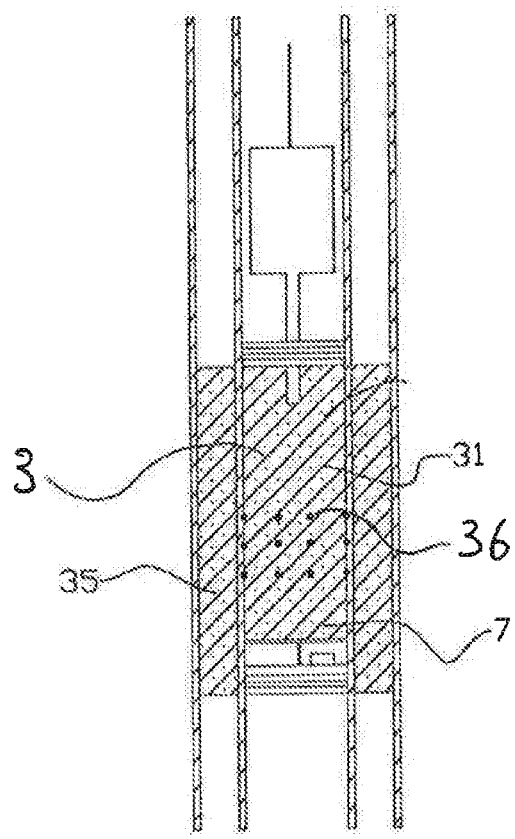
FIG. 11 shows a second embodiment of a system of the present disclosure after the method of established the plug has been completed.

FIG. 11 is a situational depiction of a wellbore after the method of establishing the resin-based plug 3 is completed. In the shown embodiment the plug 3 covers the full cross-section of the wellbore, including an annulus 35 between casings in the wellbore. Flow access between the inside of the inner casing and the annulus is enabled by means of plurality of perforations 36 created by means of a not shown casing perforation member, such as a perforation gun, as will be understood by a person skilled in the art.

The present disclosure provides a system and a method for establishing a resin-based plug 3 within a wellbore with improved physical properties, including but not restricted to, one or more of: compressive strength, tensile strength, permeability, flexural strength, rupture elongation, etc. compared to conventional cement plugs. The system and method of the present disclosure allow for improved accuracy in forming a plug in a predetermined location and/or over a shorter time period compared to conventional cement plugs. The system and method of the present disclosure enable the formation of a resin-based plug 3 which is able to withstand wellbore conditions with improved durability, improved reliability, and a reduced risk of plug failure compared to conventional cement-based plugs.

It should be noted that the above-mentioned embodiments illustrate rather than limit the disclosure, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements.

The mere fact that certain measures are recited in mutually different dependent claims does not indicate that a combination of these measures cannot be used to advantage.

The invention claimed is:

1. A method of establishing a cement plug in an annular region between a first casing and a second casing in a well wherein the method comprises the steps of:
    perforating the first casing to open a flow path to the annular region;
    providing a magnetorheological cementitious slurry;
    positioning a magnetic field inducing member inside the first casing;
    inducing, via the magnetic field inducing member, a magnetic field for affecting the physical properties of the magnetorheological cementitious slurry and for defining a lower boundary for the cement plug;
feeding the magnetorheological cementitious slurry into the annular region through a perforation in the first casing; and
impeding the mobility of the magnetorheological cementitious slurry within the first casing such that the magnetorheological cementitious slurry enters the annular region via the perforation in the first casing, and impeding the mobility of the magnetorheological cementitious slurry in the annular region by exposing it to the magnetic field such that the magnetorheological cementitious slurry may consolidate substantially at the lower boundary without the need for a base device in the annular region.

2. The method according to claim 1, further comprising the step of:
setting a base device in the first casing.

3. The method according to claim 1, wherein the method further comprises the step of:
feeding the magnetorheological cementitious slurry into the annular region such that when the magnetorheological cementitious slurry is hardened, flow is blocked entirely through both the first casing and through the second casing.

4. The method according to claim 1, wherein the magnetic field inducing member is a first magnetic field inducing member, and wherein the method further comprises the step of:
positioning a second magnetic field inducing member in the well at a predetermined depth, a distance above the first magnetic field inducing member; and
inducing, via the second magnetic field inducing member, a magnetic field for affecting the physical properties of the magnetorheological cementitious slurry so as to define an upper boundary for the cement plug.

5. The method according to claim 1, wherein the method further comprises the step of:
stopping the magnetic field inducing means from inducing a magnetic field.

6. The method according to claim 1, wherein the method further comprises the step of:
testing the quality of the cement plug.

7. The method according to claim 6, wherein the step of testing the quality of the cement plug is at least partly performed by performing a pressure test of the cement plug from below.

8. The method according to claim 6, wherein the step of testing the quality of the cement plug is at least partly performed by performing at least one of a resistive, inductive and ultrasonic logging of the cement plug.

9. The method according to claim 1, further comprising positioning a base device inside the first casing to at least partially form a block therethrough, and wherein the perforation in the first casing is positioned above the base device in the first casing.

10. A system for establishing a cement plug in an annular region between a first casing and a second casing, the system comprising:
a first magnetic field inducing member for inducing a magnetic field from inside the first casing to define a lower boundary for the cement plug in the annular region;
a second magnetic field inducing member for inducing a magnetic field from inside the first casing to define an upper boundary for the cement plug in the annular region;
a magnetorheological cement slurry for forming the cement plug; and
a cement providing means for providing the magnetorheological cementitious slurry such that when hardened the magnetorheological cementitious slurry forms the cement plug in the annular region extending between the lower and upper boundaries defined by the first and second magnetic field inducing members, respectively.

11. The system according to claim 10, wherein the system is configured such that the magnetorheological cementitious slurry when hardened entirely blocks flow through both the first casing and through the second casing.

12. The system according to claim 10, wherein the system further comprises testing means for testing the quality of a cement plug.

13. The system according to claim 12, wherein the testing means comprises:
a barrier for setting a barrier in the well, below the cement plug, to create a confined region between the barrier and the cement plug;
a fluid reservoir for storing a fluid;
a pressurizing member for pressurizing the fluid from said fluid reservoir and for transferring the pressurized fluid into the confined region;
a pressure sensor for measuring pressure in relation to said confined testing region; and
a pressure data receiver for receiving pressure data from said pressure sensor.

14. The system according to claim 10, further comprising a base device for positioning inside the first casing to at least partially form a block therethrough.

15. A cement plug established in an annular region between a first casing and a second casing in a well, in particular by the following method:
perforating the first casing to open a flow path to the annular region;
providing a magnetorheological cementitious slurry;
positioning a magnetic field inducing member inside the first casing;
inducing, via the magnetic field inducing member, a magnetic field for affecting the physical properties of the magnetorheological cementitious slurry and for defining a lower boundary for the cement plug;
feeding the magnetorheological cementitious slurry into the annular region through a perforation in the first casing;
impeding the mobility of the magnetorheological cementitious slurry in the annular region by exposing it to the magnetic field such that the magnetorheological cementitious slurry may consolidate substantially at the lower boundary without the need for a base device in the annular region; and
positioning a base device inside the first casing to at least partially form a block therethrough, and wherein the perforation through which the magnetorheological cementitious slurry is fed is above the base device in the first casing.

16. The cement plug according to claim 15, wherein the cement plug further fills an inner region of the first casing substantially corresponding in depth to the annular region.

17. The cement plug according to claim 15, wherein the cement plug comprises a length of the first casing substantially covered by the cement of the cement plug, wherein the length of the first casing is substantially intact, apart from one or more perforations.

* * * * *